US012592371B2

(12) United States Patent
Belmont et al.

(10) Patent No.: US 12,592,371 B2
(45) Date of Patent: Mar. 31, 2026

(54) NON-INTRUSIVE LASER-BASED TECHNIQUE FOR MONITOR AND CONTROL OF PROTEIN DENATURATION ON SURFACES

(71) Applicants: Erica Belmont, Laramie, WY (US);
Franco Basile, Fort Collins, CO (US);
James Rundel, Laramie, WY (US);
Andrew Goodenough, Laramie, WY
(US)

(72) Inventors: Erica Belmont, Laramie, WY (US);
Franco Basile, Fort Collins, CO (US);
James Rundel, Laramie, WY (US);
Andrew Goodenough, Laramie, WY
(US)

(73) Assignee: UNIVERSITY OF WYOMING,
Laramie, WY (US)

( * ) Notice: Subject to any disclaimer, the term of this
patent is extended or adjusted under 35
U.S.C. 154(b) by 204 days.

(21) Appl. No.: 18/427,601

(22) Filed: Jan. 30, 2024

(65) Prior Publication Data

US 2025/0172496 A1 May 29, 2025

Related U.S. Application Data

(62) Division of application No. 17/556,349, filed on Dec.
20, 2021, now Pat. No. 11,887,830, which is a
(Continued)

(51) Int. Cl.
*H01J 49/04* (2006.01)
*G01N 1/44* (2006.01)
(Continued)

(52) U.S. Cl.
CPC ............ *H01J 49/0418* (2013.01); *G01N 1/44*
(2013.01); *G01N 21/59* (2013.01);
(Continued)

(58) Field of Classification Search
None
See application file for complete search history.

(56) References Cited

U.S. PATENT DOCUMENTS 5,989,451 A * 11/1999 Lemieux ............ C09K 19/0225
349/196
10,420,608 B2 * 9/2019 Miao ..................... A61B 18/20
(Continued)

FOREIGN PATENT DOCUMENTS

GB 2326233 12/1998

OTHER PUBLICATIONS

Y. Zhang, B. Fonslow, B. Shan, M. Baek and J. Yates, "Protein
Analysis by Shotgun/Bottom-up Proteomics," Chemical Reviews,
vol. 113, No. 4, pp. 2343-2394, 2013.
(Continued)

*Primary Examiner* — Andrew Smyth
(74) *Attorney, Agent, or Firm* — Patterson + Sheridan,
LLP

(57) ABSTRACT

A method and apparatus for monitoring and/or controlling
the extent of denaturation and/or bond cleavages of proteins
on any surface (e.g., biological tissues, biofilms, etc.). In one
embodiment, a low power laser (e.g., a 5 mW, 362 nm diode
laser) is directed through a biological sample to a photode-
tector. The sample is heated by a set of radiant heaters to
between about 220° C. and about 250° C. in a time period
of between 10 seconds to 60 seconds. The baseline trans-
missivity of the sample is monitored continuously through-
out treatment of the biological sample via continuous moni-
toring of the signal voltage detected at the photodetector.
Upon detection of increase in relative transmissivity in the
biological sample, the heating treatment is concluded and
the biological sample is removed for in situ protein identi-
fication as part of an imaging MALDI-MS measurement.

20 Claims, 9 Drawing Sheets

Related U.S. Application Data division of application No. 16/524,916, filed on Jul. 29, 2019, now Pat. No. 11,205,565.

(60) Provisional application No. 62/711,040, filed on Jul. 27, 2018.

(51) Int. Cl.

| | |
|---|---|
| *G01N 21/59* | (2006.01) |
| *G01N 33/483* | (2006.01) |
| *H01J 49/00* | (2006.01) |
| *H01J 49/16* | (2006.01) |

(52) U.S. Cl.
CPC ...... *G01N 33/4833* (2013.01); *H01J 49/0004* (2013.01); *H01J 49/0459* (2013.01); *H01J 49/164* (2013.01); *G01N 2201/0636* (2013.01)

(56) References Cited

U.S. PATENT DOCUMENTS

| | | | |
|---|---|---|---|
| 2009/0325222 | A1 | 12/2009 | Agar et al. |
| 2015/0099669 | A1* | 4/2015 | Zhang ................ G01N 33/6851 435/5 |
| 2015/0335385 | A1* | 11/2015 | Miao ...................... A61B 5/015 606/12 |
| 2018/0267065 | A1* | 9/2018 | Holick ..................... G01N 1/44 |

OTHER PUBLICATIONS

S. Patterson and R. Aebersold, "Proteomics: the first decade and beyond," Nature Genetics, vol. 33, No. 3, pp. 311-323, 2003.

L. Gillet, A. Leitner and R. Aebersold, "Mass Spectrometry Applied to Bottom-Up Proteomics: Entering the High-Throughput Era for Hypothesis Testing," Annual Review of Analytical Chemistry, vol. 9, No. 1, pp. 449-472, 2016.

R. Zhou and F. Basile, "Convective-heating thermal decompositio/digestion of peptides and proteins on surfaces," Journal of Analytical and Applied Pyrolysis, vol. 127, pp. 451-460, 2017.

R. Caprioli, T. Farmer and J. Gile, "Molecular Imaging of Biological Samples: Localization of Peptides and Poteins Using MALDI-TOF MS," Anal. Chem., vol. 69, pp. 4751-4760, 1997.

E. Seeley and R. Caprioli, "Molecular imaging of proteins in tissues by mass spectrometry," PNAS, vol. 105, 2008.

R. Lattimer, M. Polce and C. Wesdemiotis, "MALDI-MS analysis of pyrolysis products from a segmented polyurethane," Journal of Analytical and Applied Pyrolysis, vol. 48, No. 1, pp. 1-15, 1998.

R. Lattimer, "Mass spectral analysis of low-temperature pyrolysis products from poly(tetrahydrofuran)," Journal of Analytical and Applied Pyrolysis, vol. 57, No. 1, pp. 57-76, 2001.

"J. Norris and R. Caprioli", "Analysis of Tissue Specimens by Matrix-Assisted Laser Desorption/Ionization Imaging Mass Spectrometry in Biological and Clinical Research,""Chemical Reviews, vol. 113, pp. 2309-2342, 2013."

D. López-Ferrer, J. Capelo and J. Vazquez, "Ultra Fast Trypsin Digestion of Proteins by High Intensity Focused Ultrasound," Journal of Proteome Research, vol. 4, No. 5, pp. 1569-1574, 2005.

E. Patel, M. Clench, A. West, P. Marshall, N. Marshall and S. Francese, "Alternative Surfactants for Improved Efficiency of In Situ Tryptic Proteolysis of Fingermarks," Journal of the American Society for Mass Spectrometry, vol. 26, No. 6, pp. 862-872, 2015.

R. Zhou and F. Basile, "Plasmonic Thermal Decomposition/Digestion of Proteins: A Rapid On-Surface Protein Digestion Technique for Mass Spectrometry Imaging," Analytical Chemistry,, vol. 89, No. 17, p. 8704-8712, 2017.

S. Zhang and F. Basile, "Site-Specific Pyrolysis-Induced Cleavage at Aspartic Acid Residue in Peptides and Proteins," Journal of Proteome Research, vol. 6, pp. 1700-1704, 2007.

F. Basile, S. Zhang, S. Kandar and L. Lu, "Mass Spectrometry Characterization of the Thermal Decomposition/Digestion (TDD) at Cysteine in Peptides and Proteins in the Condensed Phase," Journal of the American Society for Mass Spectrometry, vol. 22, pp. 1926-1940, 2011.

R. Aebersold and D. Goodlett, "Mass Spectrometry in Proteomics," Chemical Reviews, pp. 269-296, 2001.

C. Lopez de Laorden, A. Beloqui, L. Yate, J. Cavo, M. Puigivila, J. Llop and N. Reichardt, Nanostructured Indium Tin Oxide Slides for Small-Molecule Profiling and Imaging Mass Spectrometry of Metabolites by Surface-Assisted Laser Desorption Ionization MS, Journal of Analytical Chemistry, vol. 87, No. 1, pp. 431-440, 2015.

R. Kitamura, L. Pilon and M. Jonasz, "Optical constants of silica glass from extreme ultraviolet to far infared at near room temperature," Applied Optics, vol. 46, No. 33, pp. 8118-8133, 2007.

R. Parkin, "A note on the extinction coefficient and absorptivity of glass," Solar Energy, vol. 114, pp. 196-197, 2015.

A. Vogel and V. Venugopalan, "Mechanisms of Pulsed Laser Ablation of Biological Tissues," Chemical Reviews, vol. 103, No. 2, pp. 577-644, 2003.

R. Agah, J. Pearce, A. Welch and M. Motamedi, "Rate process model for arterial tissue thermal damage: Implications on vessel photocoagulation," Lasers in Surgery and Medicine, vol. 15, No. 2, pp. 176-184, 1994.

T. Wood, "Lethal Effects of High and Low Temperatures on Unicellular Organisms,"Advances in Biological and Medical Physics, vol. 4, pp. 119-165, 1956.

G. Derbyshire, D. Bogen and M. Unger, "Thermally Induced Optical Property Changes in Myocardium at 1.06um," Lasers in Surgery and Medicine, vol. 10, pp. 28-34, 1990.

R. Agah, P. Motamedi, E. Dalmia, L. Ettedgui, L. Song and J. Spears, "Potential Role of Collagen in Optical Behavior of Arterial Tissue During Laser Irradiation," Proceedings of SPIE—Laser-Tissue Interaction, vol. 1202, pp. 246-252, 1990.

A. Gandjbakhche, G. Weiss, R. Nossal and R. Bonner, "Photon path-length distributions for transmission through optically turbid slabs," Physical Review E, vol. 48, No. 2, pp. 810-818, 1993.

R. Agah, D. Sheth and M. Motamedi, "Effect of coagulation on laser light distribution in myocardial tissue," Proceedings of SPIE—Diagnostic and Therapeutic Cardiovascular Interventions, vol. 1425, pp. 172-180, 1991.

R. Agah, A. Gandjbakhche, M. Motamedi, R. Nossal and R. Bonner, "Dynamics of temperature dependent optical properties of tissue: dependence on thermally induced alteration," IEEE Transactions on Biomedical Engineering, vol. 43, No. 8, pp. 839-846.

J. Decorato, B. Chen and R. Sierra, "Subcutaneous adipose tissue response to a non-invasive hyperthermic treatment using a 1,060 nm laser," Lasers in Surgery and Medicine, vol. 49, No. 5, pp. 480-489, 2017.

S. Jacques and S. Prahl, "Modeling optical and thermal distributions in tissue during laser irradiation," Lasers in Surgery and Medicine, vol. 6, No. 6, pp. 494-503, 1987.

H. Ao, D. Xing, H. Wei, H. Gu, G. Wu and J. Lu, "Thermal coagulation-induced changes of the optical properties of normal and adenomatous human colon tissues in vitro in the spectral range 400-1100 nm," Physics in Medicine and Biology, vol. 53, No. 8, pp. 2197-2206, 2008.

A. Nilsson, C. Sturesson, D. Liu and S. Andersson-Engels, "Changes in spectral shape of tissue optical properties in conjunction with laser-induced thermotherapy," Applied Optics, vol. 37, No. 7, pp. 1256-1267, 1998.

J. Sanchez-Ruiz, "Protein kinetic stability," Biophysical Chemistry, vol. 148, No. 1, pp. 1-15, 2010.

B. Cillero-Pastor and R. Heeren, [1]B. Cillero-Pastor and R. M. A. Heeren, "Matrix-Assisted Laser Desorption Ionization Mass Spectrometry Imaging for Peptide and Protein Analyses: A Critical Review of On-Tissue Digestion," Journal of Proteome Research, vol. 13, No. 2, pp. 325-335, 2014.

M. Croseclose, M. Andersson, W. Hardesty and R. Caprioli, "Identification of proteins directly from tissue: in situ tryptic digestions coupled with imaging mass spectrometry," Journal of Mass Spectrometry, vol. 42, No. 2, pp. 254-262, 2007.

F. Mellon, "Mass Spectrometry: Principles and Instrumentation," in Encyclopedia of Food Sciences and Nutrition (Second Edition), Oxford, Academic Press, 2003, pp. 3739-3749.

(56) References Cited

OTHER PUBLICATIONS

Omega Engineering, "High Watt Density, Quartz-Faced Infrared Radiant Panel Heaters," 2018 [Online]. Available: https://www.omega.com/pptst/QC_QH_HEATERS.html#description. [Accessed May 28, 2018].

W. M. Haynes, CRC Handbook of Chemistry and Physics, 95th Edition, CRC Press, 2014.

S. Jacques and M. Gaeeni, "Thermically induced changes in optical properties of heart,"Images of the Twenty-First Century. Proceedings of the Annual International Engineering in Medicine and Biology Society, vol. 4, pp. 1199-1200, 1989.

Rundel, James A., Design, Implementation, and Modeling of a Radiative Heating Apparatus for Rapid Thermal Decomposition/ Digestion of Biological Samples, M.S., Mechanical Engineering, Aug. 2018.

Office Action for U.S. Appl. No. 16/524,916 dated Apr. 21, 2021.

* cited by examiner

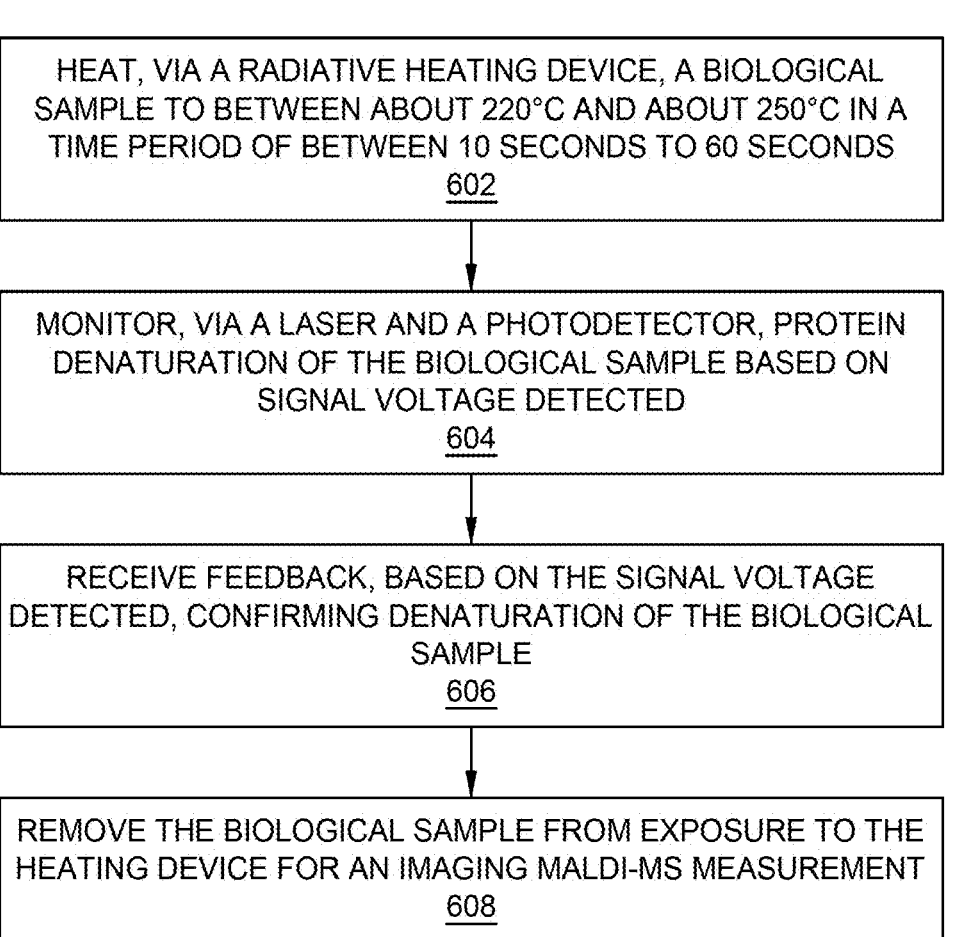

600

HEAT, VIA A RADIATIVE HEATING DEVICE, A BIOLOGICAL
SAMPLE TO BETWEEN ABOUT 220°C AND ABOUT 250°C IN A
TIME PERIOD OF BETWEEN 10 SECONDS TO 60 SECONDS
602

MONITOR, VIA A LASER AND A PHOTODETECTOR, PROTEIN
DENATURATION OF THE BIOLOGICAL SAMPLE BASED ON
SIGNAL VOLTAGE DETECTED
604

RECEIVE FEEDBACK, BASED ON THE SIGNAL VOLTAGE
DETECTED, CONFIRMING DENATURATION OF THE BIOLOGICAL
SAMPLE
606

REMOVE THE BIOLOGICAL SAMPLE FROM EXPOSURE TO THE
HEATING DEVICE FOR AN IMAGING MALDI-MS MEASUREMENT
608

FIG. 6

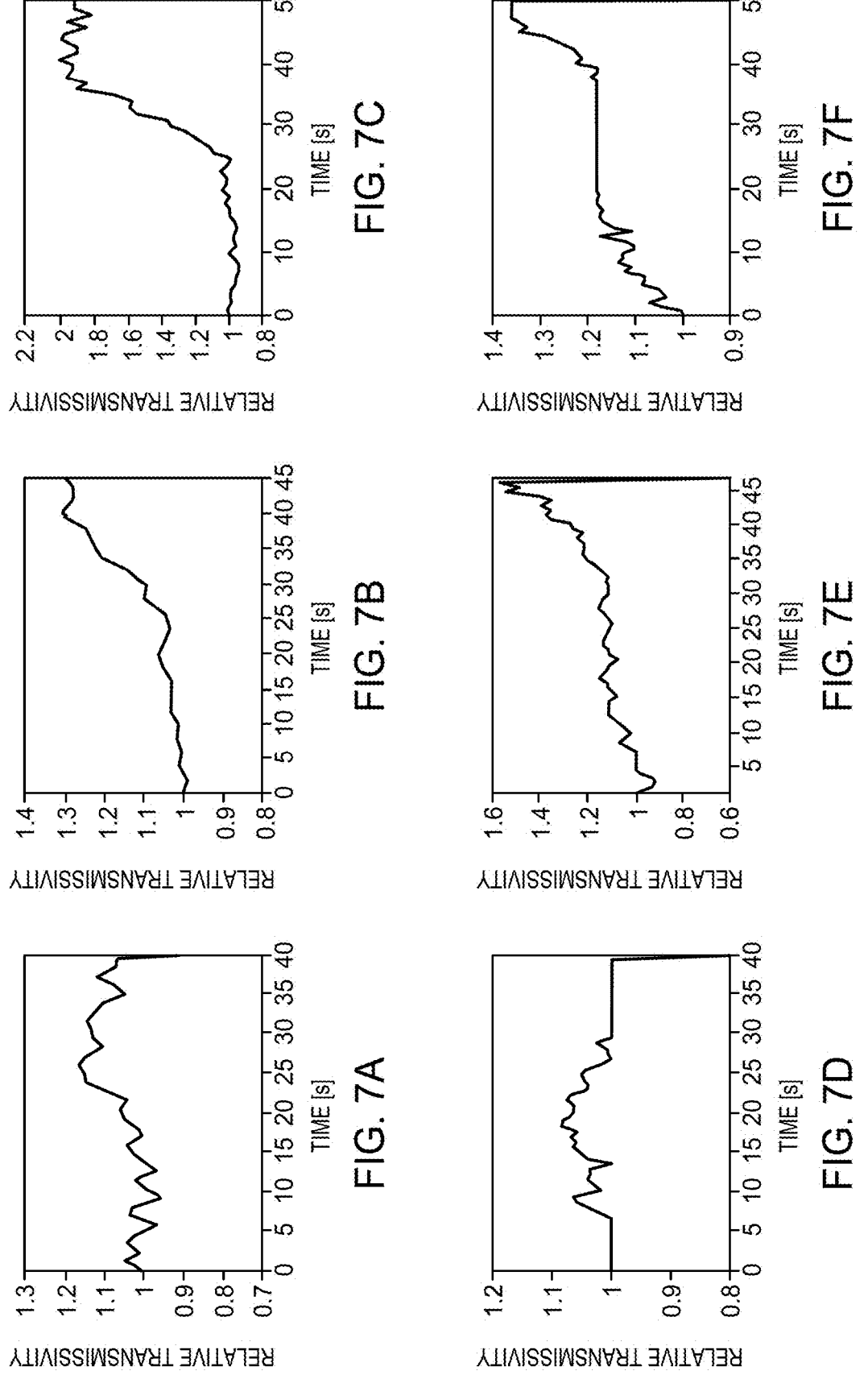

NON-INTRUSIVE LASER-BASED TECHNIQUE FOR MONITOR AND CONTROL OF PROTEIN DENATURATION ON SURFACES

CROSS-REFERENCE TO RELATED APPLICATIONS

This application is a divisional of U.S. patent application Ser. No. 17/556,349, filed Dec. 20, 2021, which is a divisional of U.S. patent application Ser. No. 16/524,916, filed Jul. 29, 2019, all of which claim priority to U.S. Provisional Patent Application No. 62/711,040, filed Jul. 27, 2018, and are herein incorporated by reference in their entirety.

GOVERNMENT RIGHTS

This invention was made with government support under Award #1611538 awarded by the National Science Foundation. The government has certain rights in the invention.

BACKGROUND

Field

Embodiments of the present disclosure generally relate to controlling protein denaturation. More specifically, aspects of the disclosure relate to a non-intrusive, laser-based technique for monitoring and controlling denaturation and/or bond cleavages of proteins on any surface (e.g., biological tissues, biofilms, etc.).

Description of the Related Art

Generally, the field of proteomics seeks to identify and quantify proteins and their functions within a proteome. Bottom-up proteomics is a common approach in the field of proteomics that identifies and characterizes proteins based on the peptides and amino acids that are released from the protein during proteolysis (e.g., the breakdown of proteins and peptides into amino acids). Peptides are readily ionized and fragmented, making the bottom-up proteomics approach amenable to tandem mass spectrometry (MS/MS) analysis, which utilizes collision induced dissociation (CID) to fragment ions from the original mass spectrum into amino acid sequences which may be used to deduce the identity of the original protein.

Matrix-assisted laser desorption/ionization mass spectrometry (MALDI-MS) is a versatile technology in applications concerning the analysis of biological samples. In MALDI-MS imaging, the biological sample is first coated with a thin layer of matrix (e.g., an organic acid that facilitates ionization of compounds within the sample) and then irradiated with a laser. Following irradiation, molecules are desorbed and ionized. In some cases, the molecules are separated by time-of-flight (TOF) mass analysis. MALDI-MS imaging technology can analyze intact biological samples, which enables the preservation of the spatial distribution of molecules within the biological sample.

Recent developments in MALDI-MS technology have enabled analysis of higher mass molecules. However, proteins with a molecular weight greater than 25 dKa and formalin-fixed paraffin-embedded (FFPE) samples remain difficult to image using MALDI-MS technology.

Traditional solutions for imaging and analysis of larger proteins and FFPE samples include a digestion process (e.g., decomposition/digestion) to break down the proteins into smaller, easier to detect peptides. The digestion process is used to obtain sequence information from the original protein. The decomposition/digestion of the original molecules present in the biological sample is performed prior to MS analysis.

In some cases, decomposition/digestion has conventionally been accomplished through an enzymatic digestion process (e.g., with an enzyme such as tryspin). However, a drawback to the enzymatic digestion process is the relatively slow reaction time for decomposition/digestion, as the conventional digestion process occurs on the scale of hours. Additionally, the enzymatic digestion process occurs under regulated conditions of atmosphere, temperature, and hydration. Further, the enzymatic digestion process, which is conducted in solution or at high hydration conditions, can lead to delocalization of products, resulting in decreased fidelity in product locations and distributions during MALDI-MS imaging.

In other cases, as an alternative solution to enzymatic digestion for imaging and analysis of larger proteins and FFPE samples, the decomposition/digestion process can be performed by thermal digestion. In particular, thermal digestion includes convective heating of biological samples without regulated conditions for atmosphere or hydration during digestion. Despite reducing the time for digestion/decomposition and the potential for product delocalization of the biological sample, there are several drawbacks associated with convective-based thermal digestion including the potential for contamination, mass transport from the sample, uneven heating, and disruption of the sample at high gas flow rates. Further, without controlling the extent of denaturation by thermal digestion, there is an uncertainty as to how long and severe a digestion/denaturation treatment should be performed, which can result in extensive trial and error to determine conversion conditions for each type of biological sample. Also, intrusive techniques for monitoring protein conversion (e.g., thermocouples) during thermal treatment can interfere with the effectiveness of the thermal treatment.

There is a need for a method and apparatus that non-intrusively monitors and controls protein denaturation on surfaces and overcomes the drawbacks and deficiencies of traditional approaches. Further, there is a need to uniformly and reproducibly heat biological samples for MALDI-MS imaging.

SUMMARY

The present disclosure generally relates to a non-intrusive laser-based technique for monitoring and controlling protein denaturation on surfaces. In particular, a laser (e.g., a low powered laser emitting wavelengths about 625 nm to about 700 nm) is directed through a biological sample (e.g., a tissue sample, biofilm, etc.) to a photodetector while the biological sample is heated by radiant heater(s) (e.g., radiant heating device). During the treatment process of the biological sample, the baseline transmissivity of the biological sample is monitored continuously based on the signal voltage detected at the photodetector. Upon a significant increase in sample transmissivity, the thermal treatment is ended because transmissivity has been found to correlate to thermal digestion. For example, once the transmissivity of the biological sample increases and begins to equilibrate, this indicates the conclusion of digestion of the biological sample. After analysis of the signal voltage detected at the photodetector and determining that the biological sample has reached the conclusion of digestion, the biological sample(s) is removed.

In one embodiment, a method of controlling protein denaturation is provided. The method includes heating, via a radiant heater, a biological sample to a temperature between about 220° C. and about 250° C. for a time period between about 10 seconds and about 60 seconds; monitoring, via a laser and a photodetector, protein denaturation of the biological sample based on a signal voltage detected; receiving feedback, based on the signal voltage detected, confirming denaturation of the biological sample; and removing the biological sample from exposure to the heating device.

In another embodiment, an apparatus is provided. The apparatus includes a heating system including: a plurality of radiant heaters; a temperature controller in communication with the plurality of radiant heaters; a stage positioned adjacent to the plurality of radiant heaters; a plurality of glass panels disposed on the stage; and a radiation heat shield moveable between a first position and a second position, the second position disposed between the plurality of radiant heaters and the stage. The apparatus further includes a transmissivity monitoring system to monitor and control an extent of decomposition/digestion of one or more biological samples, which includes a laser for monitoring protein denaturation of the biological sample and a photodetector to monitor an intensity of a laser beam from the laser, and record, via an output voltage, the intensity of the laser. The photodetector monitors an intensity of a laser beam from the low-powered laser, and records, via an output voltage, the intensity of the laser beam, and the transmissivity monitoring system includes a data acquisition device for monitoring output from the photodetector in real-time.

In another embodiment, a method of controlling protein denaturation is provided. The method includes heating, via a radiant heater, a biological sample to a temperature between about 220° C. and about 250° C. for a time period between about 10 seconds and about 60 seconds; monitoring, via a laser and a photodetector, protein denaturation of the biological sample based on a signal voltage detected; receiving feedback, based on the signal voltage detected, confirming denaturation of the biological sample; removing the biological sample from exposure to the heating device for an imaging matrix-assisted laser desorption/ionization mass spectrometry (MALDI-MS) measurement; and generating a MALDI-MS image of the biological sample.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 6 is a flow chart for a method of monitoring and controlling the extent of protein denaturation.

FIGS. 7A-7F illustrate data from continuous monitoring of biological samples in a slide configuration.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

In the following, reference is made to embodiments of the disclosure. However, it should be understood that the disclosure is not limited to specific described embodiments. Instead, any combination of the following features and elements, whether related to different embodiments or not, is contemplated to implement and practice the disclosure.

Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

Figure 1:
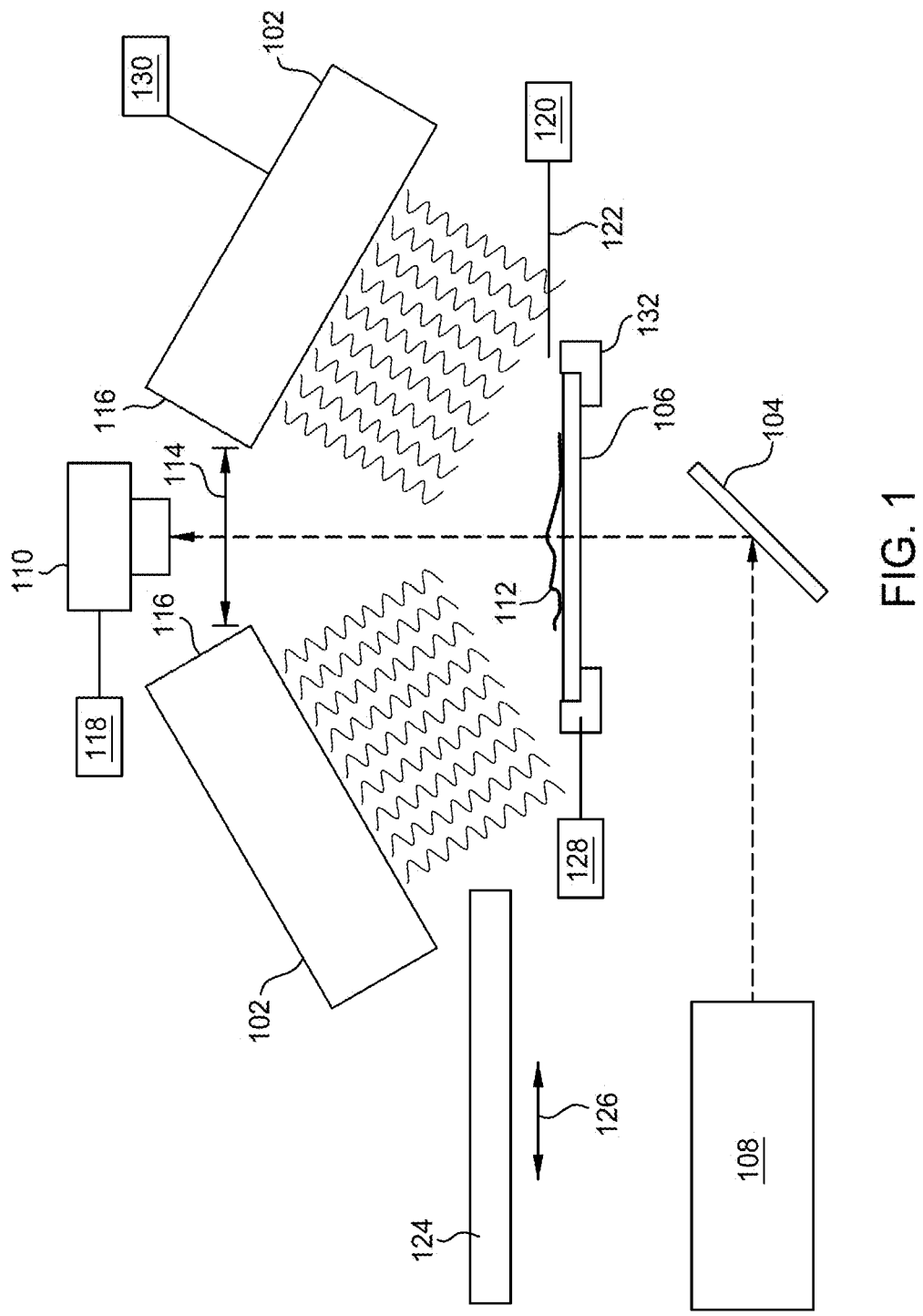
FIG. 1 illustrates a schematic of an integrated heating and monitoring system.

FIG. 1 illustrates an example schematic of an integrated heating and monitoring system 100. The example schematic illustrates the integrated heating and monitoring system 100 including radiant heaters 102 (e.g., infrared heaters), a mirror 104, a slide 106, a laser 108 (e.g., 635 nm laser), and a photodetector 110.

As illustrated, a biological sample 112 (e.g., a tissue sample) can be mounted to the slide 106 and positioned within the system 100. In one example, the biological sample 112 has a thickness of about 5 μm to about 20 μm. For example, the thickness of the biological sample 112 can be between about 8 μm and about 16 μm, for example, between about 10 μm and about 14 μm, such as about 12 μm. The biological sample 112 can have a section size of about 8 cm by about 12.5 cm. In some cases, the biological sample 112 can be larger or smaller than the section size of 8 cm by 12.5 cm. The biological sample 112 can be heated by the radiant heaters 102 to a temperature of between about 220° C. and about 250° C. for duration of between about 10 seconds and about 60 seconds. In some cases, the biological sample can be heated to temperatures and durations as described in U.S. Patent Publication No. 2010/0044560, U.S. Pat. Nos. 8,637,325, and 9,396,921, which are incorporated herein by reference in therein entirety. 240/480 V OMEGA QH-061060-T radiant heaters can be utilized as the heaters 102. In other implementations, the radiant heaters 102 emit in the infrared range between 2.5-6 μm with a maximum heat flux of 60 W/m². In one implementation, the radiant heaters 102 are positioned at an angle to heat the biological sample 112. In the illustrated example having two radiant heaters 102, the radiant heaters 102 can be angled between about 10° and about 30° from a horizontal plane toward the biological sample 112. For example, the each of the radiant heaters 102 may be angled about 20° from a horizontal plane toward the biological sample 112. In some cases, the integrated heating and monitoring system 100 can include one radiant heater 102 or more than two radiant heaters 102. The radiant heaters 102 are also in communication with a temperature controller 130. The temperature controller 130, such as a PID controller or the like, are operable to control the amount of heat generated by the radiant heaters 102. In some cases, the integrated heating and monitoring system can include convective heating device(s) for thermal digestion, such that monitoring the biological sample 112 can prevent disadvantages associated with simply heating via convective heaters.

The system 100 further includes a shield 124 which is moveable along a horizontal plane 126. The shield 124 is coupled to an actuator or track and is moveable between an external position (shown) and an isolating position which is located between the heaters 102 and the slide 106. The shield 124 is fabricated from a material which is selected to reflect and/or absorb heat, for example, a metallic material which has a low coefficient of thermal conductivity. In one embodiment, the shield 124 is fabricated from a metal foil, such as aluminum foil or the like. In other embodiments, the shield 124 is an aluminized woven silica heat barrier (e.g., Thermo-Tec 13500) exterior and an aluminum honeycomb grid core (e.g., with 6.35 mm cells). In operation, when a sample denaturation process is performed, the shield 124 is moved into the isolating position to stop heating of the biological sample 112 to prevent overheating of the biological sample 112. By reflecting heat away from the biological sample 112, further denaturation of the biological sample 112 can be substantially reduced or prevented. It is believed that by utilizing the shield 124, overheating of the biological sample 112 may be avoided and more precise thermal control of the biological sample 112 may be achieved.

The system 100 also includes a gas source 120 which is coupled to a conduit 122. The gas source 120 may be an inert gas source, such as a nitrogen source, an argon source, a helium source, or the like. The conduit 122 extends from the gas source 120 to a region adjacent to the slide 106. For example, the conduit 122 extends from the gas source 120 to a region between the slide 106 and the radiant heaters 102. In this manner, gas can be delivered to the region immediately above the slide 106 to create an inert environment substantially surrounding the biological sample 112 during heating of the biological sample 112.

The system 100 also includes a stage 132. The stage 132 is sized to support the slide 106 positioned thereon during heating of the biological sample 112. In one embodiment, the stage 132 is coupled to an actuator 128 which is operable to elevate the stage 132 and change the proximity of the stage 132 relative to the radiant heaters 102. The actuator 128 may be any suitable actuator, such as a mechanical actuator, an electromagnetic actuator, a pneumatic actuator, a linear actuator or the like. In one example, the stage 132 is a steel cage attached to a 12 mm diameter steel post (e.g., ThorLabs TR3) and mounted to a steel base (e.g., ThorLabs BA2) with a post holder (e.g., ThorLabs PH3). The stage 132 may further be constructed of mild steel with a cut-out in the center. The cut-out in the center of the stage 132 enables optical access to the sample from both sides. Additional details of an example stage are illustrated in FIG. 3. In some cases, a set of glass panels can be mounted to the stage 132. The set of glass panels can support the slide 106, upon which the biological sample 112 is mounted. The glass panels are described in greater detail with reference to FIG. 2 and FIGS. 4A and 4B. In one example, the slide 106 can be an indium-tin oxide (ITO) coated slide that creates a transparent conductive layer on the slide 106.

The stage 132 may be positioned at a desired proximity to the radiant heaters 102 which is believed to provide for improved heating control during heat processing of the biological sample 112. In one example, the stage 132, after having the slide 106 with the biological sample 112 positioned thereon, may be elevated by actuation via the actuator 128 and positioned in an elevated process position. Upon receiving input of sample denaturation, the actuator 128, which may be in communication with a data acquisition device 118 (described hereinafter) and the temperature controller 130, may lower the slide 106 to reduce or minimize heat exposure of the biological sample 112 while providing for increased spacing for positioning of the shield 124 between the slide 106 and the radiant heaters 102.

Additionally, a gap 114 of about 0.5 cm and about 2 cm, such as about 1 cm extends between facing edges 116 of the opposing radiant heaters 102. The gap 114 enables passage of electromagnetic energy (e.g. laser energy) from the laser 108 to pass through the slide 106 and biological sample 112 and continue propagating between the radiant heaters 102 to the photodetector 110. The gap 114, which is wide enough to enable propagation of a beam of electromagnetic energy therethrough, remains narrow enough to prevent external environmental factors from adversely affecting the biological sample 112 during heat processing of the biological sample 112. For example, the gap 114 positions the heaters 102 relative to the biological sample 112 such that temperature non-uniformities of the sample heating environment are reduced or eliminated.

Further, the heating process of the biological sample 112 can be monitored. In some implementations, the radiant heaters 102 heat one or more biological samples 112. For example, a plurality of biological samples can be heated by the radiant heaters 102 such that each biological sample in the plurality of biological samples is individually heated via the radiant heaters 102. As illustrated, electromagnetic energy propagates from a laser 108 and passes through the biological sample 112 mounted on the slide 106 via redirection by the mirror 104. In one example, the laser 108 is a low powered red laser, such as a 635 nm laser. In another example, the laser 108 is a 5 mW, 632 nm diode laser. The laser 108 can emit wavelengths in the range of about 625 nm to about 700 nm. Once the electromagnetic energy generated by the laser 108 passes through the biological sample 112, the laser energy can be detected by the photodetector 110. In one example, the photodetector 110 is a photodiode detector and can be equipped with a 635 nm band pass filter integrated with the heating system. The photodetector 110 can monitor and/or record the intensity of the laser energy passing through the biological sample 112. For example, the photodetector 110 can monitor and/or record the intensity of the laser energy based on the output voltage from the photodetector 110. Additionally, a data acquisition device 118, which is in communication with the photodetector 110, can monitor output from the photodetector 110. In one example, the data acquisition device 118 is a data recorder, a computer, a memory device, or the like configured to store data received and/or generated by the photodetector 110. For example, the data acquisition device 118 can monitor the output from the photodetector 110 in real-time at a sampling rate of between about 150 Hz and about 450 Hz, such as about 300 Hz. In one embodiment, the laser energy temperature and/or power is computer-controlled to ensure accurate and predictable heating of the biological sample 112.

The integrated heating and monitoring system 100 monitors the biological sample 112 for transmissivity response to the heating process. Optical diagnostics monitor, and in some cases, provide a real-time control measure for assessing the extent of protein digestion during heating. In one example, the transmissivity responses of the biological sample 112 are monitored to identify the point of digestion, which can appear during the monitoring as a sharp increase in transmissivity. For example, the relative transmissivity of biological samples 112 sharply increase through the heating process (e.g., thermal digestion), and then the relative transmissivity equilibrates near the conclusion of digestion. In such cases, the effect is believed to be a result of a reduction in average particle size, which can lead to a decreased scattering effect as described by Mie theory, as proteins in the biological sample undergo significant denaturation during the heating process. Advantageously, each biological sample 112 can be monitored and/or recorded because the decreased scattering effect is compositionally sensitive. After the point of digestion is identified, in some cases, the biological sample can be removed from the system 100 for MALDI-MS imaging.

As described above, the laser 108 emits electromagnetic energy, such as a laser beam, which passes through the biological sample 112 via the mirror 104. In one example, the mirror 104 is angled to redirect a horizontal laser beam from the laser 108 to vertically pass through the biological sample 112 on the slide 106. In one embodiment, the laser beam's propagation path is substantially perpendicular to a major axis of the biological sample 112. During the heating process, the biological sample 112 undergoes the digestion process. The photodetector 110 monitors the heating process and, based on results obtained during the monitoring, determine when the biological sample 112 has reached the point of digestion (e.g., for MALDI-MS imaging). For example, the photodetector 110 can monitor the intensity of the laser beam as the laser beam passes through the biological sample 112. When the relative transmissivity of the biological sample 112 increases, the biological sample 112 is ready to be removed because in some cases, an increase in relatively transmissivity is due to the biological sample 112 reaching the point of digestion from the heating process.

In one implementation, the system 100 is an open system and the biological sample 112 heated by the radiant heaters 102 is exposed to an ambient environment. In other implementations, nitrogen gas can be used to create an inert shroud over the surface of the slide 106. For example, in order to create an inert gas flow over the slide 106, nitrogen flow can be metered with a rotameter and directed through stainless steel tubing to a brass elbow with an inner diameter of approximately 2 cm. The elbow can be packed with steel wool to create a uniform flow profile and can be positioned approximately 1 cm upstream (e.g., above) of the slide 106.

In some cases, temperatures generated by the radiant heaters 102 are controlled via a feedback loop to the temperature controller 130 (e.g., an OMEGA CN740). The temperature controller 130 can read the temperature from a K-type thermocouple embedded in a quartz thermowell in the heaters 102.

The heaters 102 may be suspended from a rail system superstructure via an aluminum suspension rod fastened to the rail system and radiant heater by friction rod clamps. The suspension system enables each radiant heater 102 to move laterally along the rail system and rotate around the suspension rod. Further, each radiant heater 102 can be individually positioned related to the biological sample 112, which enables a higher degree of control in the magnitude and location of radiant energy received by the biological sample 112.

Figure 2:
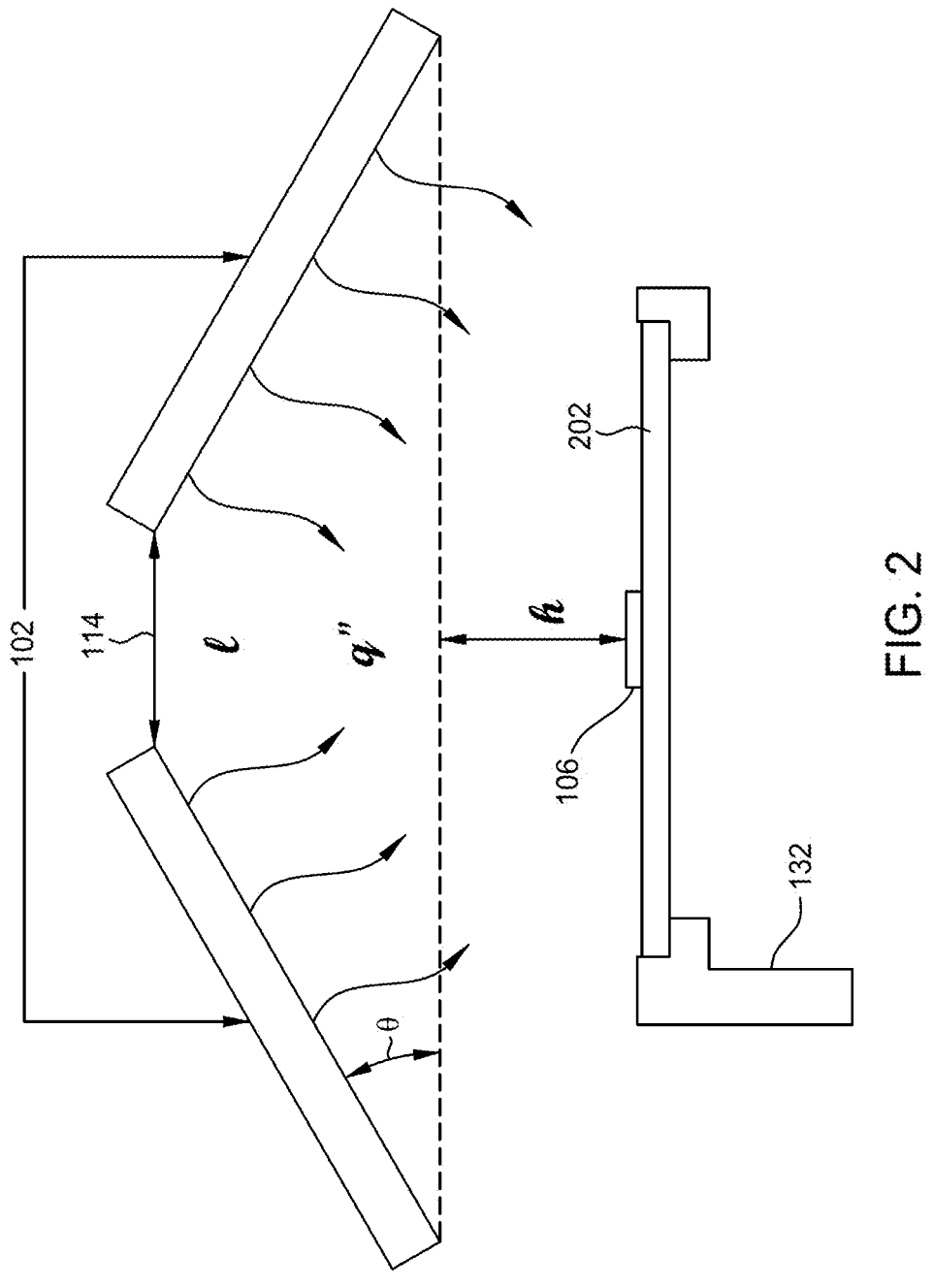
FIG. 2 illustrates a schematic side view of the radiant heating system.
Figure 3:
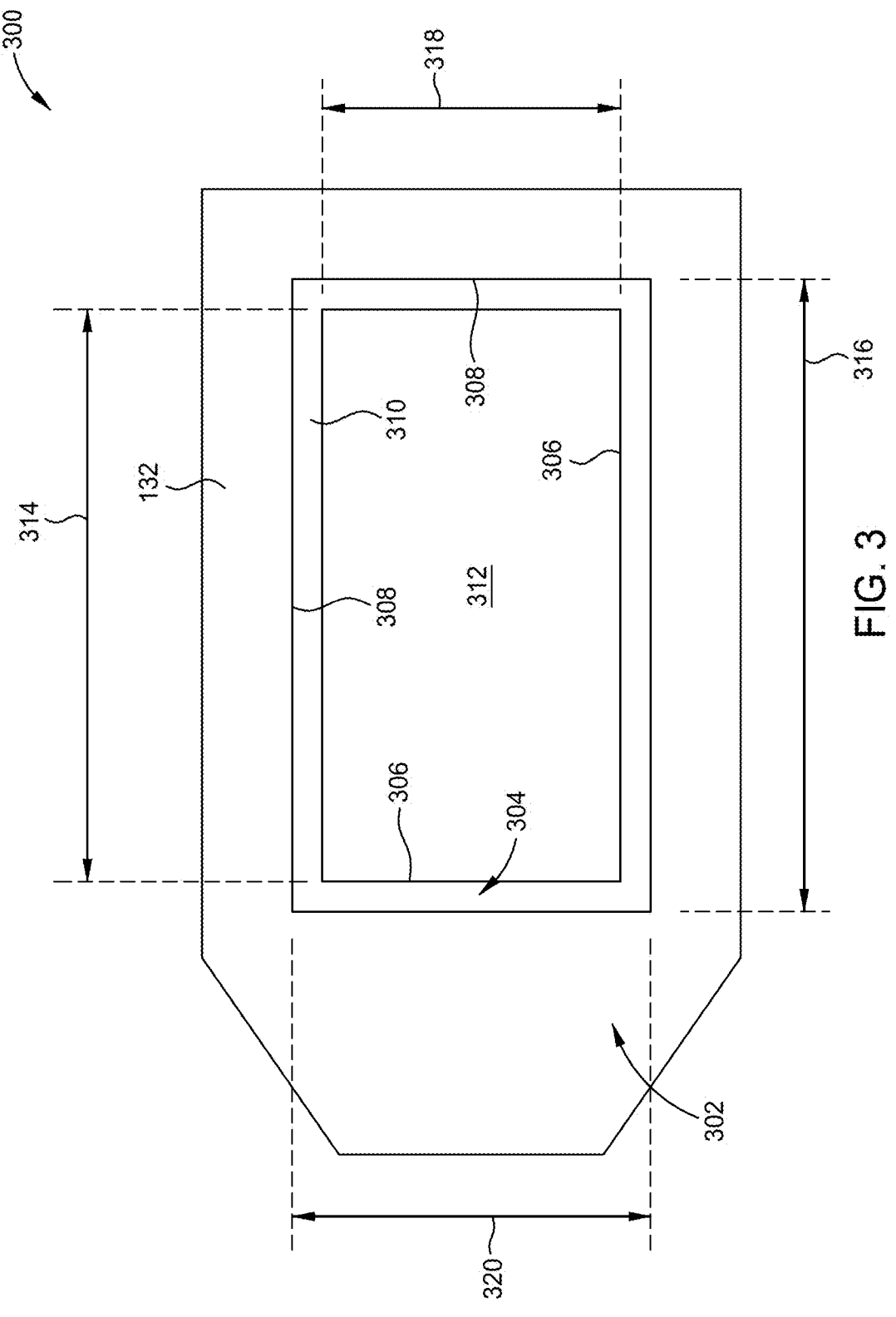
FIG. 3 illustrates a plan view of a stage.

FIG. 2 illustrates a simplified schematic of the radiant heating system. The heater design is included in the radiant heating system in order to uniformly heat an area the same size as a MALDI plate (10.16 cm by 15.24 cm) and optically monitor the heating process. In other cases, a radiant heating system can include a single radiant heater to heat and optically monitor biological sample(s). The system further includes glass panels 202 which are positioned on the stage 132. The glass panels 202 are substantially quadrilateral in shape and are sized to fit on the stage 132 and provide a support for the slide 106. In one embodiment, the glass panels 202 are fabricated from a glass material, a quartz material, or other suitable material which is substantially transparent to laser energy at various desired wavelengths and which retains sufficient mechanical integrity at temperatures above about 200° C.

As illustrated, the dual heater design incorporates multiple variables (e.g., h, l, q'', and $\ominus$) including slide and heater position. The variable h refers to the separation distance between the radiant heaters 102 and the stage 132. For example, in a dual radiant heater 102 design, the distance h between the radiant heaters 102 and the stage 132 is between about 50 mm and about 150 mm, such as between about 75 mm and about 125 mm, for example about 90 mm. The variable l refers to the distance of the gap 114 between interior edges of the two radiant heaters 102. As described above, the distance (e.g., gap 114) between the radiant heaters 102 is between about 0.5 cm and about 2 cm, such as about 1 cm. The variable q'', which is heat flux per unit area and refers to the degree of heat from radiant heaters 102 to the biological sample 112. For example, a radiant heater temperature can be between about 550° C. and about 800° C., such as between about 600° C. and about 725° C., for example, about 675° C. in order to heat the biological sample 112 to a temperature of between about 220° C. and about 250° C. in a time period of between about 10 seconds and about 60 seconds. The variable $\ominus$ refers to the angle of the radiant heater 102 from horizontal toward the biological sample 112 such that the radiant heater 102 can achieve substantially uniform and complete heating of the biological sample 112. For example, the angle of each radiant heater can be between about 10° and about 30°, such as about 20°.

The incorporation of the multiple variables enables highly customizable configurations. Further, sample heating rates can be calculated based on heat flux and view factor. In some cases, the combination of the heat flux and view factor can effectively describe the amount of energy received by the biological sample 112.

FIG. 3 illustrates a plan view of the stage 132. The stage 132, which is sized to accommodate one or more glass panels 202 therein which support the slide 106, is fabricated from metallic material as previously described. An aperture 312 is formed in the stage 132. The aperture 312 is an opening within the stage 132 which has a substantially quadrilateral morphology. In one embodiment, the aperture 312 is rectangular. However, it is contemplated that other quadrilateral shapes, such as a square, may be suitable for the aperture 312. It is also contemplated that the aperture 312 may exhibit other non-quadrilateral morphologies, such as circular or the like.

The stage 132 includes a top surface 302 and a plurality of surfaces 308 which at least partially define the aperture 312. A ledge 310, which defines a surface 304, is recessed below the top surface 302 and extends inward in all directions from the plurality of surfaces 308. The surface 304 of the ledge 310 extends inward from the plurality of surfaces 308 to a plurality of surfaces 306. The plurality of surfaces 306 further define the aperture 312.

A major axis magnitude 314 of the surfaces 306 is between about 60 mm and about 80 mm, such as about 70 mm. A major axis magnitude 316 of the surfaces 308 is between about 65 mm and about 85 mm, such as about 75 mm. A minor axis magnitude 318 of the surfaces 306 is between about 35 mm and about 55 mm, such as about 40 mm. A minor axis magnitude 320 of the surfaces 308 is between about 40 mm and about 60 mm, such as about 50 mm.

Figure 4A:
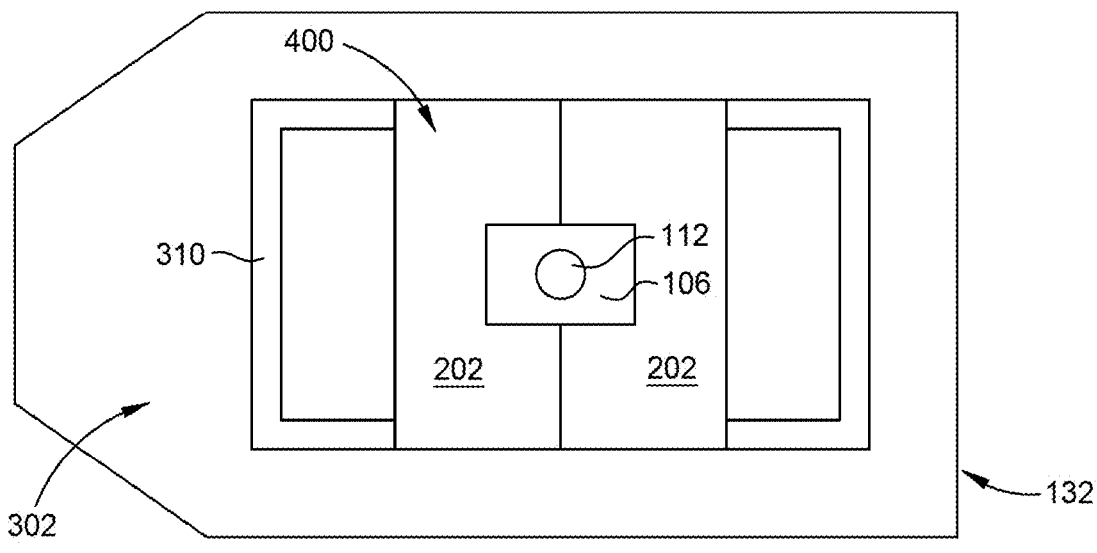
FIGS. 4A and 4B illustrate example slide mounting configurations.

FIG. 4A illustrates an example slide configuration 400 of glass panels 202 mounted to the stage. As depicted in the slide configuration 400, the slide 106 rests on top of two panels 202 which are positioned on the ledge 310 of the stage 132. The panels 202 are positioned immediately adjacent to one another and, in one embodiment, are in contact with one another such that the slide 106 is fully supported with the panels 202 extending underneath the slide 106.

Figure 4B:
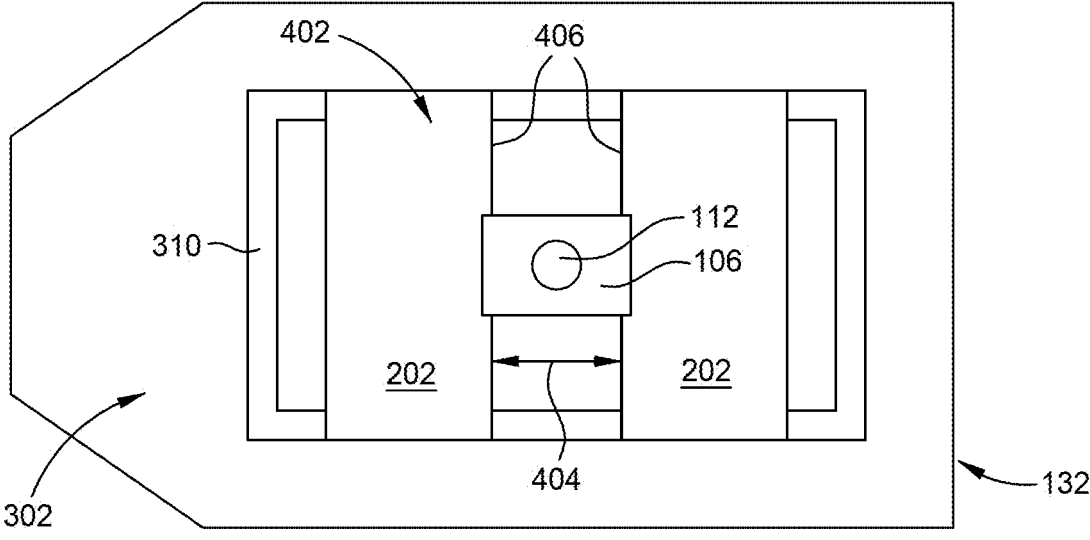

FIG. 4B illustrates an example slide configuration 402 of glass panels 202 mounted to the stage 132. As depicted in the slide configuration 402, the slide 106 is supported on two opposing edges 406 of the glass panels 202 which are positioned on the ledge 310 of the stage 132. The panels 202 are positioned in a spaced apart orientation with a gap 404 extending between the opposing edges 406. In such a configuration, the majority of the slide 106 backside is exposed to ambient air.

Biological samples 112 monitored in the slide configuration 400 (FIG. 4A) exhibit a significantly dampened heating rate relative to the slide configuration 402 (FIG. 4B). The slide configuration 402 enables a faster heating rate and a shorter digestion time for the biological sample 112.

In some cases, the portion of the slide 106 that is supported by the glass panels 202 in the slide configuration 402 can heat at a different rate than the portion of the slide 106 that is exposed to ambient air. In such cases, the slide configuration 402 can result in a non-uniform heating profile over the slide 106. However, the slide configuration 402 may be advantageously employed for heating, monitoring, and controlling denaturation of smaller biological samples because the smaller biological samples are believed to remain unaffected by the uneven heating which may result from slide configuration 402.

Figure 5A:
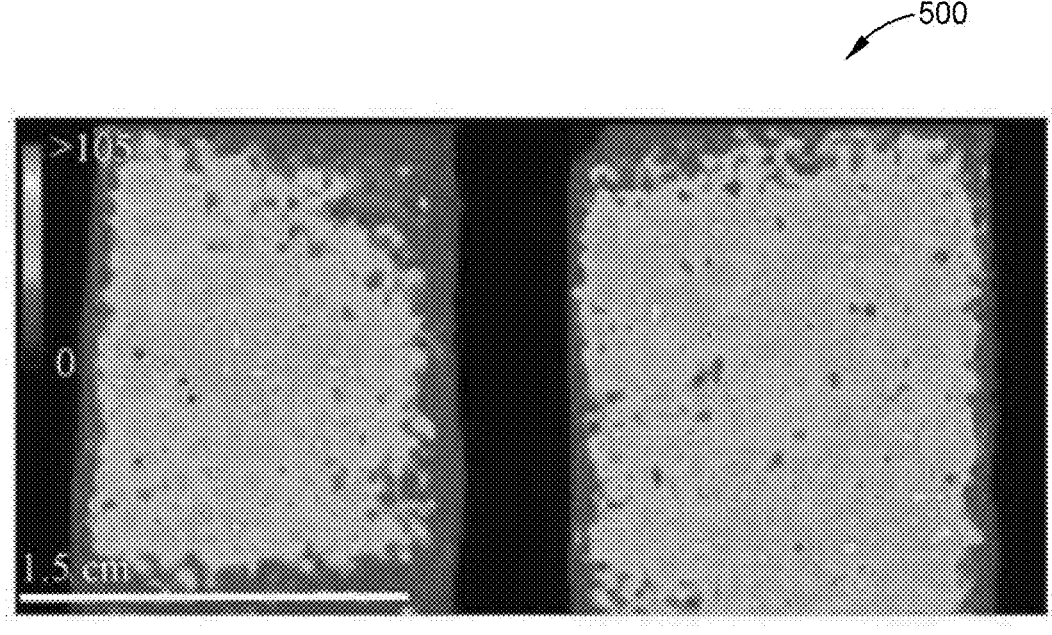
FIGS. 5A and 5B illustrate example profiles of thermal digestion of biological samples using the slide configuration of FIG. 4A and FIG. 4B, respectively.
Figure 5B:
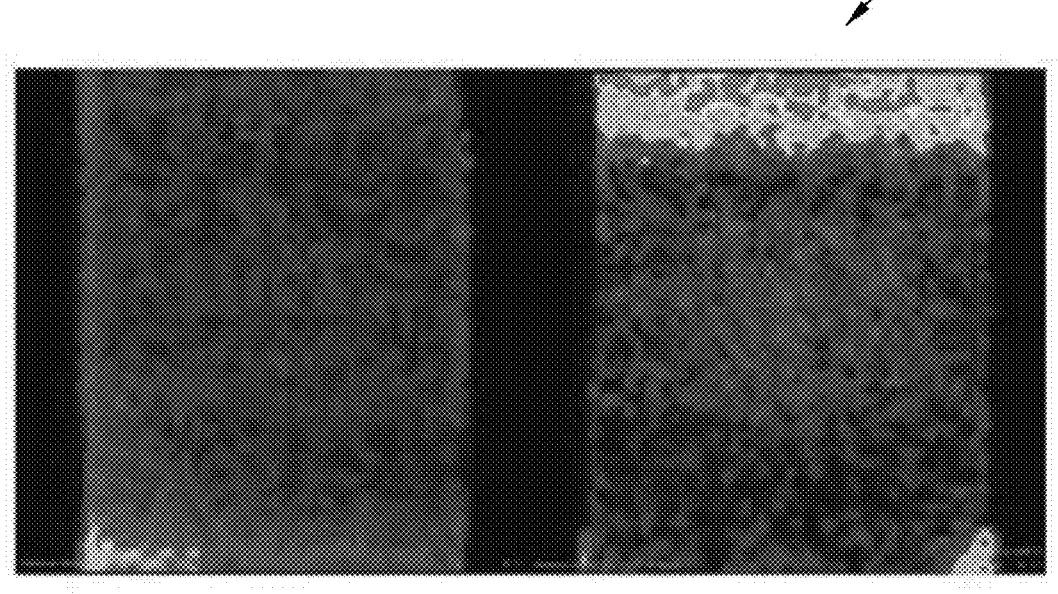

FIGS. 5A and 5B illustrate example profiles of thermal digestion of biological samples using the slide configuration 400 of FIG. 4A and the slide configuration 402 of FIG. 4B, respectively. In particular, FIGS. 5A and 5B depicts the MALDI-MS image profile of thermal digestion for biological sample that has been analyzed by MALDI-MS using the slide configuration 400 and slide configuration 402, respectively. In particular, the MALDI-MS image is of m/z=1299 from lysozyme digestion for a biological sample in a slide configuration 400 (FIG. 5A) and a slide configuration 402 (FIG. 5B).

As illustrated by the MALDI-MS image profiles, the portion of the slide 106 supported by the glass panels 202 in the slide configuration 400 (FIG. 5A) experiences a different heating rate and maximum temperature than the portion of the slide 106 that is suspended in the slide configuration 402 (FIG. 5B). Further, the effects of different heat rates can be localized to the portion of the slide 106 directly supported by the glass panels 202. As such, smaller biological samples can be advantageously utilized in the slide configuration 402.

FIG. 6 depicts a method 600 of monitoring and controlling the extent of sample denaturation. As shown, the method begins at operation 602 where an integrated heating and monitoring system can heat via a radiant heating device a biological sample to between about 220° C. and about 250° C. in a time period of between about 10 seconds and about 60 seconds. At operation 604, the integrated heating and monitoring system monitors, via a laser and a photodetector, protein denaturation of the biological sample based on signal voltage detected by the photodetector. At operation 606, the integrated heating and monitoring system receives feedback, based on the signal voltage detected, confirming denaturation of the biological sample. At operation 608, the integrated heating and monitoring system can remove the biological sample from exposure to the heating device. In some case, the operation can include removing the biological sample for an imaging MALDI-MS measurement, and generating a MALDI-MS image of the biological sample after the biological sample has been removed.

FIGS. 7A-7F illustrates data from an implementation of continuous monitoring of biological samples in the slide configuration 400. FIGS. 7A-7C illustrates data corresponding to muscle tissue samples at 40 seconds, 45 seconds, and 50 seconds, respectively. FIGS. 7D-7F illustrates data corresponding to brain tissue samples at 40 seconds, 45 seconds, and 50 seconds, respectively.

As illustrated in the data, the continuous monitoring provides real-time analysis of transmissivity of a biological sample to predict when significant digestion occurs. FIGS. 7A-7F illustrate that there is a sharp increase in transmissivity corresponding to digestion time. While the magnitude of change varies between the trials and tissue samples, there is a qualitatively abrupt change in transmissivity near the point of digestion, which is indicative of a critical change in tissue structure or properties.

As depicted in the data of FIGS. 7A-7F, prior to the point where digestion begins to occur and the transmissivity rapidly increases, most of the trials display a general increase in the relative transmissivity. This particular result is not expected because conventional denaturation detection techniques typically suggest that thermal treatment of tissues at elevated temperatures result in a decrease in transmissivity and increase in the scattering coefficient for multiple tissue types. One possibility to account for the unexpected result is that in the implementation of continuous monitoring, the tissues are subjected to higher temperatures within the first two seconds of heating. The higher temperatures applied during the implementation of continuous monitoring as described herein can cause even more extensive denaturation of proteins than conventional techniques and can outweigh the effects of coagulation on scattering light, contributing to the general increase in transmissivity seen throughout the heating process. Further, the biological samples are exposed to high initial temperatures before the primary heating process while the biological samples are protected by the heat shield 124, which can be result in pre-coagulation of the tissue and mitigate any initial effect of coagulation during the transmissivity monitoring.

Figures 8A, 8B, 8C:
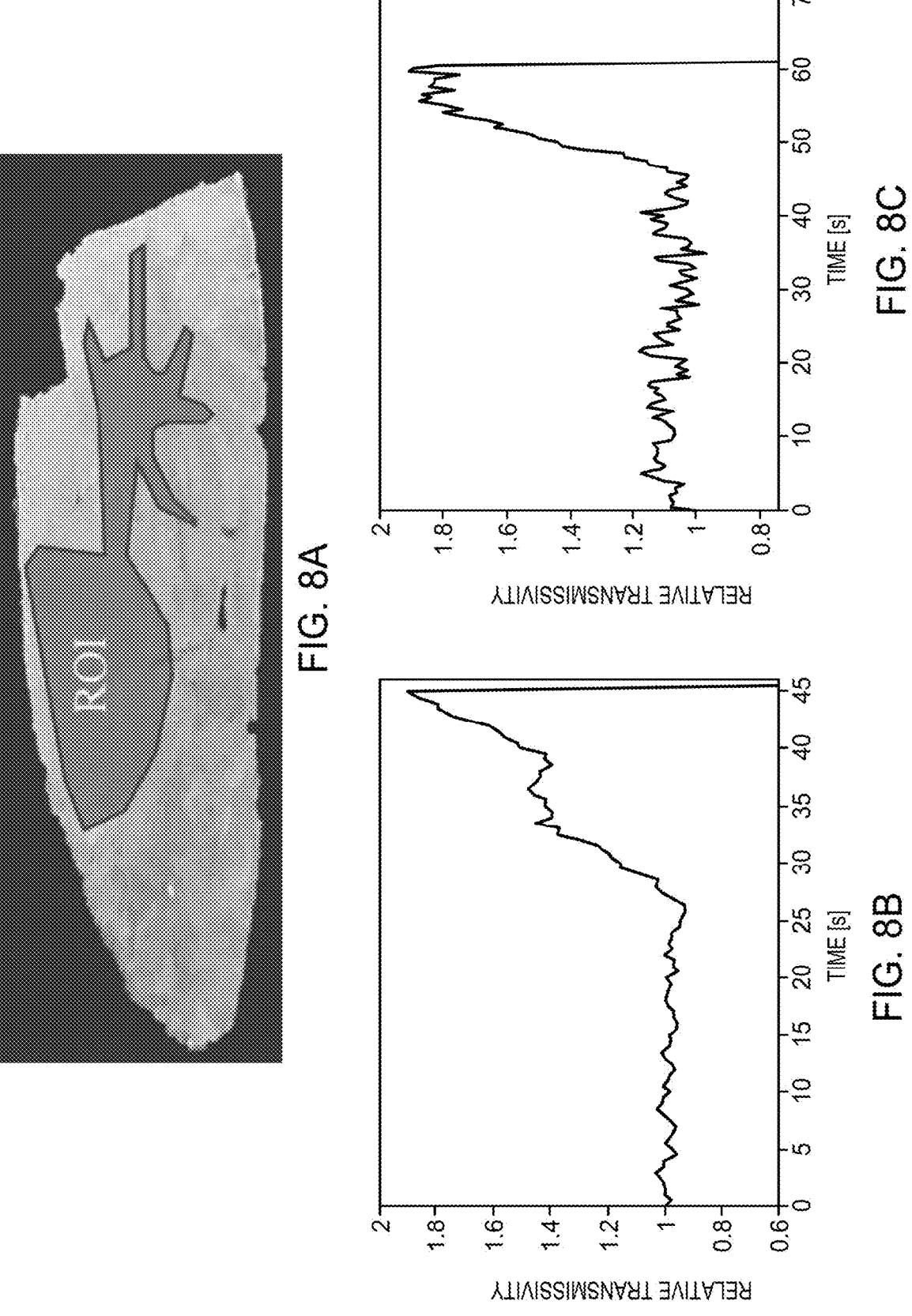
FIGS. 8A-8C illustrates data indicating transmissivity response is not uniform across a tissue sample.
Figure 9A:
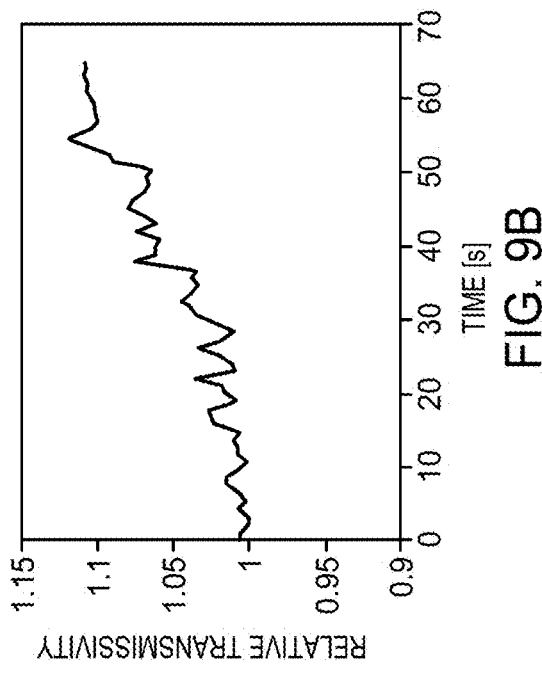
FIGS. 9A-9D illustrates data indicating transmissivity response is not uniform across different types of biological samples.
Figure 9B:
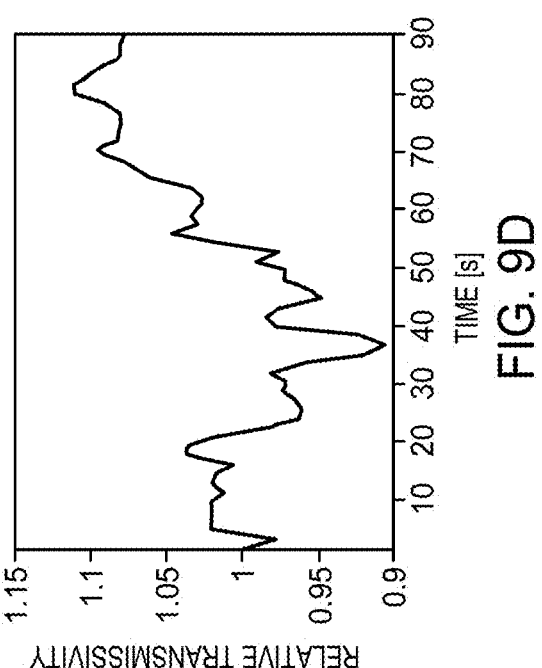
Figure 9C:
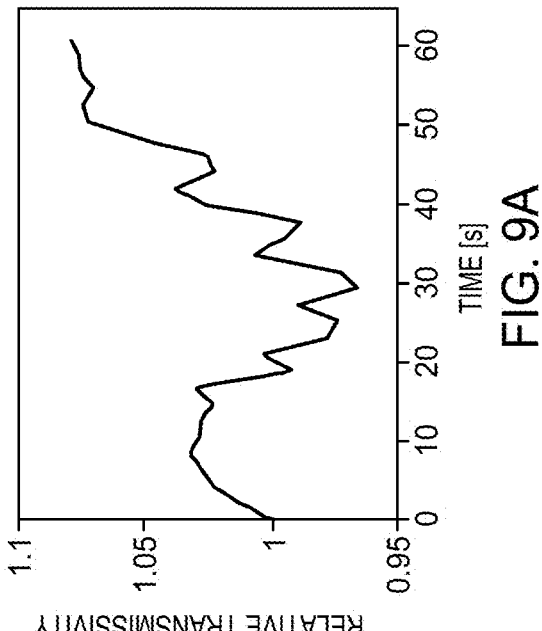
Figure 9D:
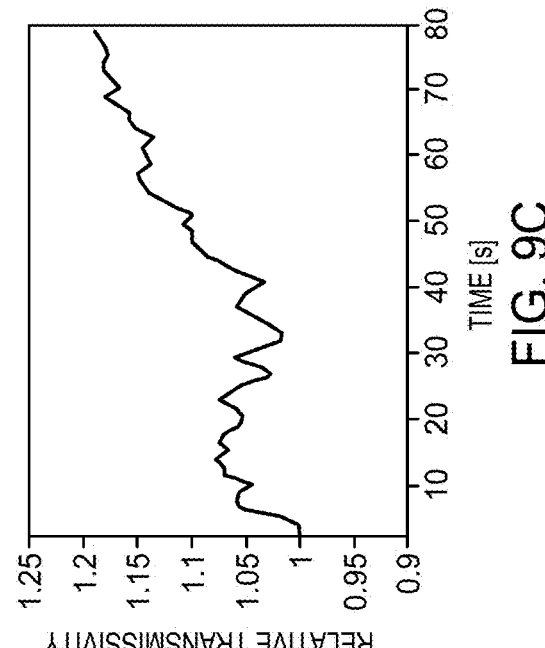

FIGS. 8A-8C illustrates data indicating transmissivity response is not uniform across a tissue sample. In particular, FIGS. 8A-8C depicts relative transmissivity response of different regions within a brain tissue sample. A region of interest (ROI) can be visually identified for monitoring within a set of tissue samples (FIG. 8A). During the monitoring, two traces were taken. A first trace of the brain tissue at 45 seconds (FIG. 8B) reflects the relative transmissivity response for ROI. A second trace of the brain tissue at 60 seconds (FIG. 8C) reflects relative transmissivity response for a different region of the brain tissue other than the ROI.

FIGS. 9A-9D illustrates data indicating transmissivity response is not uniform across different types of biological samples. During testing, the transmissivity response was monitored for four types of proteins: lysozyme, cytochrome C, carbonic anhydrase, and BSA. Through the monitoring, the test results indicate that lysozyme and cytochrome C have ideal digestion times of approximately 55 seconds. Carbonic anhydrase and BSA have relatively prolonged digestion in comparison to lysozyme and cytochrome C. In particular, carbonic anhydrase and BSA exhibit signs of digestion after 55 seconds and have an ideal digestion time of approximately 65 seconds.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed here.

Furthermore, although embodiments disclosed herein may achieve advantages over other possible solutions or over the prior art, whether or not a particular advantage is achieved by a given embodiment is not limiting of the scope of the present disclosure. Thus, the aspects, features, embodiments, and advantages described are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

While the foregoing is directed to embodiments of the present disclosure, other and further embodiments of the disclosure may be devised without departing from the basic scope thereof, and the scope thereof is determined by the claims that follow.

What is claimed is:

1. An apparatus, comprising:
 a plurality of radiant heaters opposing one another and having a gap therebetween;
 a photodetector disposed between the plurality of radiant heaters and adjacent the gap;
 a stage disposed opposite the photodetector;
 a plurality of glass panels disposed on the stage;
 a laser;
 a mirror; and
 an electromagnetic propagation path extending from the laser to the mirror, through the stage and the plurality of glass panels, and through the gap to the photodetector, wherein the photodetector is configured to:
  monitor an intensity of electromagnetic radiation generated by the laser; and
  record, via an output voltage, the intensity of the laser.

2. The apparatus of claim 1, wherein the electromagnetic propagation path is substantially perpendicular to a major axis of a biological sample positioned on the stage.

3. The apparatus of claim 1, wherein the laser is adapted to emit the electromagnetic radiation that passes through a biological sample positioned on the stage.

4. The apparatus of claim 1, wherein the mirror is angled to direct the electromagnetic radiation vertically through a biological sample positioned on the stage.

5. The apparatus of claim 1, wherein the gap is between about 0.5 cm and about 2 cm.

6. The apparatus of claim 1, wherein the plurality of radiant heaters comprises two radiant heaters maintained at a temperature of between about 550° C. and about 800° C.

7. The apparatus of claim 1, wherein the plurality of radiant heaters comprises two radiant heaters maintained at a temperature of between about 600° C. and about 725° C.

8. The apparatus of claim 7, wherein the two radiant heaters are angled between about 10° and about 30° from horizontal to the stage.

9. The apparatus of claim 1, wherein the photodetector is a photodiode detector.

10. The apparatus of claim 1, wherein the photodetector includes a 635 nm band-pass filter.

11. The apparatus of claim 1, wherein the electromagnetic radiation has a wavelength of about 625 nm to about 700 nm.

12. The apparatus of claim 1, further comprising a shield moveable between an external position and an isolating position, the isolating position disposed between the plurality of radiant heaters and the stage.

13. The apparatus of claim 12, wherein the shield is operable to thermally isolate or reflect heat away from a biological sample positioned on the stage.

14. An apparatus, comprising:
 a plurality of radiant heaters opposing one another and having a gap therebetween;
 a photodetector disposed between the plurality of radiant heaters and adjacent the gap;
 a stage disposed opposite the photodetector;
 a plurality of glass panels disposed on the stage;
 a slide supported by the plurality of glass panels;
 a laser;
 a mirror; and
 an electromagnetic propagation path extending from the laser to the mirror, through the stage and the plurality of glass panels, and through the gap to the photodetector, wherein the photodetector is configured to:
  monitor an intensity of electromagnetic radiation generated by the laser; and
  record, via an output voltage, the intensity of the laser.

15. The apparatus of claim 14, wherein the electromagnetic propagation path is substantially perpendicular to a major axis of a biological sample disposed on the slide.

16. The apparatus of claim 14, wherein the laser is adapted to emit the electromagnetic radiation that passes through a biological sample disposed on the slide.

17. The apparatus of claim 14, wherein the mirror is angled to direct the electromagnetic radiation vertically through a biological sample disposed on the slide.

18. The apparatus of claim 14, wherein two radiant heaters of the plurality of radiant heaters are angled between about 10° and about 30° from horizontal to the stage.

19. The apparatus of claim 14, further comprising a shield moveable between an external position and an isolating position, the isolating position disposed between the plurality of radiant heaters and the stage, the shield operable to thermally isolate or reflect heat away from a biological sample positioned on the stage.

20. An apparatus, comprising:

a plurality of radiant heaters opposing one another and having a gap therebetween;

a photodetector disposed between the plurality of radiant heaters and adjacent the gap;

a stage disposed opposite the photodetector, the plurality of radiant heaters comprising two radiant heaters angled between about 10° and about 30° from horizontal to the stage;

a plurality of glass panels disposed on the stage;

a shield moveable between an external position and an isolating position, the isolating position disposed between the plurality of radiant heaters and the stage;

a laser;

a mirror; and an electromagnetic propagation path extending from the laser to the mirror, through the stage and the plurality of glass panels, and through the gap to the photodetector, wherein the photodetector is configured to:

monitor an intensity of electromagnetic radiation generated by the laser; and record, via an output voltage, the intensity of the laser.

* * * * *